United States Patent [19]

Chiulli

[11] 4,067,339
[45] Jan. 10, 1978

[54] ENTEROSTOMY RETAINER

[75] Inventor: Robert D. Chiulli, Somerville, Mass.

[73] Assignee: Medico Developments, Inc., Boxford, Mass.

[21] Appl. No.: 721,175

[22] Filed: Sept. 7, 1976

[51] Int. Cl.² .................................................. A61B 17/00
[52] U.S. Cl. ............................ 128/303 R; 24/31 C; 292/307 R; 292/320; 403/276; 403/361
[58] Field of Search .............. 24/31 C; 70/457; 128/1, 128/303 R; 292/307, 320; 403/276, 361

[56] References Cited

U.S. PATENT DOCUMENTS

| 758,099 | 4/1904 | Paradice | 285/257 |
| 1,219,046 | 3/1917 | Schultz | 292/320 |
| 1,577,678 | 3/1926 | Behrman | 292/307 R X |
| 2,670,735 | 3/1954 | Brody | 128/133 |
| 2,871,691 | 2/1959 | Bacon | 70/457 X |
| 3,730,187 | 5/1973 | Reynolds | 128/DIG. 26 X |
| 3,779,247 | 12/1973 | Nolan et al. | 128/303 R |

Primary Examiner—Channing L. Pace
Attorney, Agent, or Firm—Scott R. Foster

[57] ABSTRACT

An enterostomy retainer comprising a rigid cylindrical base portion and a flexible tubular portion extending from a first end of the base portion. The second end of the base portion and the free end of the tubular portion have interconnecting means to facilitate connection of the tubular portion free end to the cylindrical portion second end to form a closed loop.

4 Claims, 3 Drawing Figures

ENTEROSTOMY RETAINER

BACKGROUND OF THE INVENTION

1. Field of the Invention

This invention relates to surgical devices and is directed more particularly to an enterostomy retaining device.

2. Description of the Prior Art

In enterostomy procedures a bowel length is externalized by passage of a bowel loop through an opening made in the abdominal wall. The loop enterostomy requires a fixation device to maintain the bowel in its externalized position. The retention has been accomplished with various rods of synthetics or glass. Many of the devices in general use stress the bowel unevenly at its angulation or require readjustment or removal with consequent remanipulation of the traumatized area when bag placement is performed.

SUMMARY OF THE INVENTION

An object of the present invention is to provide an enterostomy retaining device which is easily applied, permits complete access to the bowel, does not stress the bowel, does not require remanipulation of the wound area, particularly during dressing and bag application, and which fulfills its function in a fail-safe manner.

Another object of the invention is to provide a device as above described which is simple and inexpensive to manufacture.

With the above and other objects in view, as will hereinafter appear, a feature of the present invention is the provision of an enterostomy retainer comprising a substantially rigid cylindrical base portion and a flexible tubular portion extending from a first end of the base portion, the second end of the base portion and the free end of the tubular portion having interconnecting means whereby the base portion second end and the tubular portion free end may be connected together to form a closed loop.

The above and other features of the invention, including various novel details of construction and combinations of parts, will now be more particularly described with reference to the accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention from which its novel features and advantages will be apparent.

DESCRIPTION OF THE PREFERRED EMBODIMENTS

Figure 1:
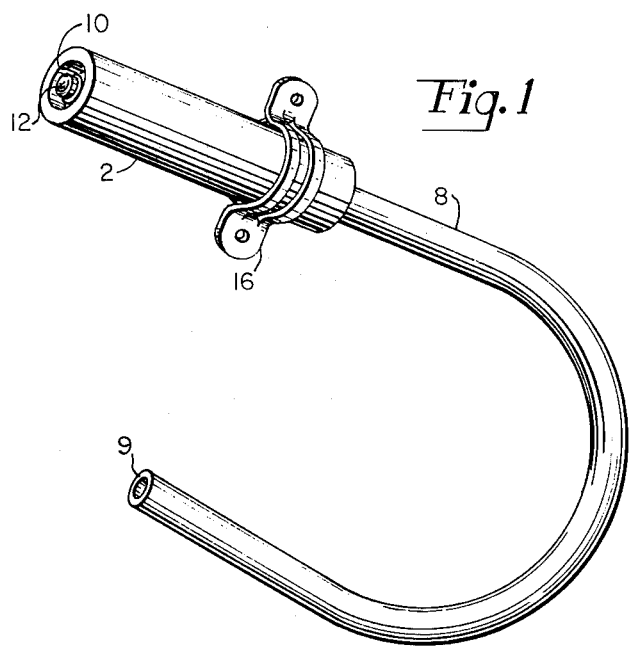
FIG. 1 is a perspective view showing one form of retainer illustrative of an embodiment of the invention.
Figure 2:
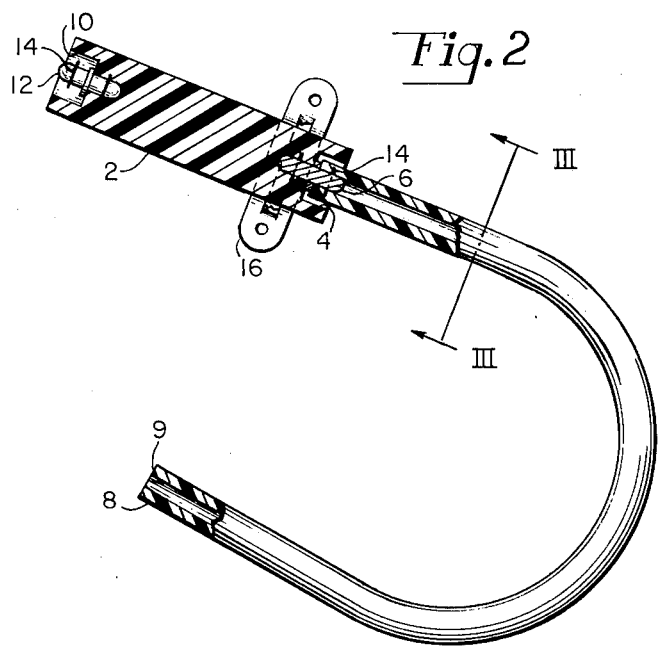
FIG. 2 is a side center line sectional view.
Figure 3:
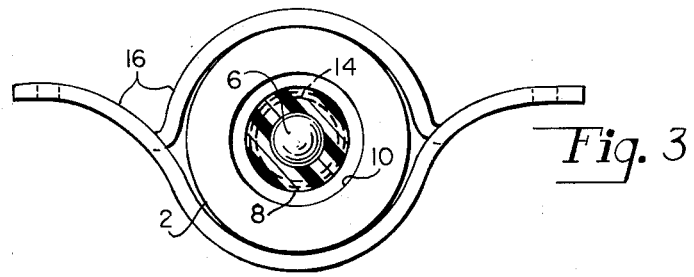
FIG. 3 is an end elevational view taken in the direction of arrow III in FIG. 2.

Referring to the drawings, it will be seen that the invention comprises a cylindrical base portion 2, which is of a substantially rigid material, such as nylon. The base portion 2 has a concavity 4 in which is disposed a first prong 6. A tubular portion 8, preferably of flexible polyvinylchloride, is fitted onto the prong 6 within the concavity 4.

The other end of the base portion 2 is provided with a recess 10 having disposed therein a second prong 12 onto which can be pressed the free end 9 of the tubular portion 8 to complete a closed loop.

The prongs 6, 12 may be metal and may be disposed one at either end. Alternatively, a single rod constituting both prongs may perform the same function. The prongs may, as another alternative, be plastic and may be molded integrally with the base portion 2. Each prong is provided with barb means 14 which engages the interior of the tubular portion and prevents accidental separation of the prong and tubular portion. Preferably, the prongs are disposed wholly within the concavity 4 and recess 10, thereby minimizing the diameter of the closed loop. The prongs may extend beyond the end of the base portion but such arrangement increases the diameter of the loop.

A stitch band 16, which may be of neoprene, is mounted on the base portion 2 which is rotatably movable within the stitch band.

In use, after an opening is made in an abdominal wall and a portion of bowel in the form of a loop is drawn through the opening, an appropriately sized device is selected. The stitch band is discarded if not desired. The base portion 2 is then inserted in the loop of the bowel so that as the bowel seeks to return beneath the abdominal wall, the base portion is positioned beneath the bowel and retains the bowel in its externalized position.

The free end of the tubular portion 8 is then pressed onto the prong 12 and retained by pressure fit and the barb 14, completing a closed loop about the bowel. Before being connected to the prong 12, the tubular portion 8 may be shortened by simply snipping off the unneeded length, whereby to provide the diameter of retainer loop desired. The diameter desired would generally be one which is small enough to fit within a bag which will subsequently cover the exposed bowel but not so small as to compress the encompassed bowel.

The retainer may be sutured to the skin by way of the stitch band if desired, the base portion 2 being rotatably movable within the stitch band after suturing of the stitch band to the skin.

The retainer may be removed by cutting the sutures, if used, cutting the tubular portion and withdrawing the base portion.

It is to be understood that the present invention is by no means limited to the particular construction herein disclosed and/or shown in the drawings, but also comprises any modifications or equivalents within the scope of the disclosure.

Having thus described my invention, what I claim as new and desire to secure by Letters Patent of the United States is:

1. An enterostomy retainer comprising a substantially rigid cylindrical portion having a smooth exterior wall and a flexible tubular portion connected to and extending from a first end of said cylindrical portion, said tube being of substantially smaller outside diameter than said cylindrical portion, a second end of said cylindrical portion having a projection extending axially outwardly from said cylindrical portion and being of a diameter smaller than the diameter of said cylindrical portion and generally complementary to the inside diameter of said tube, said projection having barb means thereon, and a free end of said tubular portion being adapted to engage and be engaged by said barb means, whereby said cylindrical portion may be placed beneath on externalized bowel to retain said bowel in the externalized position resting upon said smooth exterior wall and said free end of said tubular portion may be permanently connected to said second end of said cylindrical portion by engagement of said barb means with interior portions of said tubular portion free end to encircle said bowel and prevent loss of said retainer.

2. The invention according to claim 1 in which said projection is rigid and is integral with said cylindrical portion.

3. The invention according to claim 1 in which said cylindrical portion is provided with a stitch band, said cylindrical portion being rotatable within said stitch band.

4. The invention according to claim 1 in which said cylindrical portion is of rigid plastic and said tubular portion is of flexible plastic, and including a first projection extending axially outwardly at said first end of said cylindrical portion and being an integral part of said cylindrical portion, said second end projection being an integral part of said cylindrical portion, said first projection and said second end projection each having barb means about its periphery, said tubular portion being at one end permanently disposed on said first projection, the barb means of said first projection engaging the interior of said tubular portion, and the barb means of said second end projection being adapted to engage the interior of said free end of said tubular portion.

* * * * *